United States Patent [19]

Pall et al.

[11] Patent Number: 4,617,124
[45] Date of Patent: Oct. 14, 1986

[54] POLYMERIC MICROFIBROUS FILTER SHEET, PREPARATION AND USE

[75] Inventors: David B. Pall, Roslyn Estates; Peter J. Degen, Huntington; Thomas C. Gsell, Levittown, all of N.Y.

[73] Assignee: Pall Corporation, Glen Cove, N.Y.

[21] Appl. No.: 397,762

[22] Filed: Jul. 13, 1982

[51] Int. Cl.$^4$ .............................................. B01D 13/00
[52] U.S. Cl. ..................................... 210/638; 210/508
[58] Field of Search ............... 210/638, 503, 504, 508, 210/505, 500.1, 500.2; 427/244

[56] References Cited

U.S. PATENT DOCUMENTS

| | | | |
|---|---|---|---|
| 2,985,540 | 5/1961 | Goldbeck | 117/76 |
| 3,158,532 | 11/1964 | Pall et al. | 210/505 |
| 3,246,767 | 4/1966 | Pall et al. | 210/505 |
| 3,309,222 | 3/1967 | Caldwell | 117/138.8 |
| 3,353,682 | 11/1967 | Pall et al. | 210/505 |
| 3,684,562 | 8/1972 | Pascal | 427/296 |
| 3,817,772 | 6/1974 | Heit | 117/11 |
| 3,826,674 | 7/1974 | Schwarz | 117/62.2 |
| 3,949,124 | 4/1976 | Jilla | 428/96 |
| 3,988,157 | 10/1976 | Van Paesschen et al. | 96/87 R |
| 4,007,114 | 2/1977 | Ostreicher | 210/504 X |
| 4,049,870 | 9/1977 | Brodmann | 428/424 |
| 4,119,746 | 10/1978 | Bleyle | 427/381 |
| 4,137,110 | 1/1979 | Singh | 156/62.2 |
| 4,170,682 | 10/1979 | Beetschen | 428/267 |
| 4,214,020 | 7/1980 | Ward et al. | 427/296 |
| 4,230,573 | 10/1980 | Kilty et al. | 210/767 |
| 4,238,193 | 12/1980 | Kisaichi et al. | 8/115.5 |
| 4,293,600 | 10/1981 | Fink et al. | 427/388.5 |
| 4,305,782 | 12/1981 | Ostreicher et al. | 210/503 X |
| 4,473,475 | 9/1984 | Barnes, Jr. et al. | 210/500.2 X |
| 4,523,995 | 6/1985 | Pall et al. | 210/504 |

FOREIGN PATENT DOCUMENTS

| | | | |
|---|---|---|---|
| 2505331 | 3/1976 | Fed. Rep. of Germany | 428/424 |
| 2840765 | 3/1979 | Fed. Rep. of Germany | 117/76 |
| 2910289 | 9/1980 | Fed. Rep. of Germany | 210/505 |
| 2016943B | 10/1979 | United Kingdom | 210/503 |
| 2068432A | 8/1981 | United Kingdom | 210/503 |
| 2098590B | 11/1982 | United Kingdom | 210/503 |

*Primary Examiner*—Frank Spear
*Attorney, Agent, or Firm*—Leydig, Voit & Mayer, Ltd.

[57] ABSTRACT

Microfibrous, polymeric filter sheets and filter elements prepared therefrom comprised of a normally hydrophobic, microfibrous, polymeric web, wherein the surfaces of the microfibers making up the web are coated with a cured, precipitated, cationic, thermosetting binder resin or polymer. The filter sheet is further characterized by being hydrophilic and having a positive zeta potential.

The process for preparing such filter sheets comprises four steps:

(1) applying a first solution or dispersion of a precipitating agent to a hydrophobic web to at least partially wet the web;

(2) applying a second solution of the binder resin or polymer to the wetted web of step (1);

(3) working the wetted web of step (2) to mix the first and second solutions, thereby facilitating the precipitation of the binder resin or polymer and the distribution of the precipitated binder resin or polymer as a coating on the surface of the microfibers making up the worked web; and (4) drying and curing the coated web of step (3) to form the desired filter sheets.

The filter sheets have enhanced mechanical strength, are hydrophilic, have positive zeta potentials over the pH range of from about 3 to about 10 and typically have absolute pore ratings of from about 0.5 to about 80 micrometers.

89 Claims, No Drawings

4,617,124

POLYMERIC MICROFIBROUS FILTER SHEET, PREPARATION AND USE

TECHNICAL FIELD

The present invention relates generally to filter media, their preparation and their use in filtering fluids. More particularly, the invention relates to novel hydrophilic, microfibrous, polymeric filter sheets with greatly improved filtration efficiencies for the removal of particulates.

The function of a filter is the removal of suspended particulate material and the passage of the clarified fluid medium. A filter can achieve fluid clarification by different mechanisms. Particulate material can be removed through mechanical sieving wherein all particles larger than the pore diameter of the filter sheet are removed from the fluid. With this mechanism, filtration efficiency is controlled by the relative size of the contaminant and filter pore diameter. The efficient removal of very small particles, e.g., less than 0.1 micrometer in diameter, therefore requires filter media with very small pore sizes for removal by mechanical sieving. Such finely pored filter sheets tend to have the undesirable characteristics of high pressure drop across the filter sheet, reduced dirt capacity and shorter filter life.

A filter may also remove suspended particulate material by adsorption onto the filter surfaces. Removal of particulate material by this mechanism is controlled by the surface characteristics of (1) the suspended particulate material, and (2) the filter medium. Most suspended solids which are commonly subjected to removal by filtration are negatively charged in aqueous systems near neutral pH. This feature has long been recognized in water treatment processes where oppositely charged, cationic flocculating agents are employed to improve settling efficiencies during water clarification.

Colloidal stability theory is used to predict the interaction of electrostatically charged particles and surfaces. If the charges of a particle and the filter sheet surface are of like sign and with zeta potentials of greater than about 20 mV, mutual repulsive forces will be sufficiently strong to prevent capture by adsorption. If the zeta potentials of the suspended particles and the filter surface are small, or more desirably of opposite sign, the particles will tend to adhere to the filter pore surface with high capture efficiency. Thus, filter sheets characterized by positive zeta potentials are capable of removing, by electrostatic capture, negatively charged particles much smaller than the pores of the filter.

In addition to good particle capture characteristics, filter sheets must also have good mechanical strength and the ability to withstand high differential pressure loadings without fracturing or otherwise mechanically failing. In some applications, transients in differential pressure loading may exceed 70 pounds per square inch.

Microfibrous, polymeric webs, e.g., polypropylene webs, have a negative zeta potential in alkaline media. Accordingly, their ability to remove negatively charged suspended particulate material by adsorption is limited. Additionally, microfibrous, polymeric webs are hydrophobic in nature and, as a result, at a given applied pressure have lower fluid flow rates, than comparable hydrophilic filter sheets. Alternatively, a higher pressure drop across the hydrophobic filter sheet is required to maintain the same flow rate, an undesirable feature for filtration media.

Microfibrous, hydrophobic, polymeric webs, typically having absolute pore ratings ranging from about 1 to about 30 or 40 micrometers and in some instances as high as about 80 micrometers, have desirable features for some filtering applications including use as prefilters for removing relatively coarse particles, e.g., of from about 1 to about 30 or 40 micrometers in diameter and larger by sieving action. They have a relatively high dirt capacity and are resistant to chemical attack. Their "clean" filtering nature, i.e., low shedding characteristics, adds to their attractiveness. It would be highly desirable to be able to utilize the attractive features of these webs while enhancing their desirability and range of uses for filtering applications by rendering them hydrophilic, providing them with a positive zeta potential and improving their mechanical strength.

The present invention is directed, then, to the preparation of hydrophilic, microporous, polymeric filter sheets from normally hydrophobic, microfibrous, polymeric webs. It is also directed to the resulting filter sheets and their use. The process of this invention provides hydrophilic, mirofibrous, polymeric filter sheets with absolute pore ratings as fine as about 0.5 micrometer absolute, excellent mechanical strength, reduced pressure drops at given flow rates compared with their hydrophobic counterparts, and enhanced particulate removal efficiencies by means of electrostatic particle capture due to their positive zeta potential.

DISCLOSURE OF THE INVENTION

This invention is directed to filter media, particularly filter sheets, comprising a microfibrous, polymeric filter sheet comprised of a normally hydrophobic, microfibrous, polymeric web, wherein the surfaces of the microfibers making up the web are coated with a cured, precipitated, cationic, thermo-set binder resin or polymer. The filter sheet is further characterized by being hydrophilic and having a positive zeta potential.

The subject invention is also directed to the process for preparing such filter sheets and their use in filtration applications. The general method of preparing these filter sheets comprises four steps:

(1) applying a first solution or dispersion of a precipitating agent to a hydrophobic web comprised of polymeric microfibers to at least partially wet the web with this first solution;

(2) applying a second solution of a water-soluble, non-colloidal, cationic, thermosetting binder resin or polymer to the wetted web of step (1) above to form a web wetted with a mixture of the first solution or dispersion and the second solution;

(3) working the wetted web of step (2) above to mix the first solution or dispersion and the second solution, thereby facilitating the precipitation of the binder resin or polymer and the distribution in a uniform manner of the precipitated binder resin or polymer as a coating on the surfaces of the microfibers making up the worked web; and (4) drying the coated web of step (3) above and curing the precipitated binder resin or polymer coating to form the desired filter sheet.

The filter sheets of the subject invention typically have absolute pore ratings in the range of from about 0.5 to about 80 micrometers and are particularly useful in filtering negatively charged particles down to as low as about 0.1 micrometer or even finer, i.e., molecular dimensions. They also have enhanced mechanical strengths compared with the untreated hydrophobic webs from which they are formed.

Preferred base web materials for preparing the filter sheets of the subject invention are hydrophobic, polymeric webs comprised of microfibers of polyolefins, polyesters or polyamides. Preferred binder resins or polymers for use in this invention are the epoxide-based, water-soluble resins, such as the epoxy-functional polyamido/polyamino-epichlorohydrin resins. Particularly preferred are the epoxy-functional, polyamine-epichlorohydrins containing quaternary ammonium groups. Preferred precipitating agents may be selected from a group of synthetic, water-soluble or dispersible polymers containing anionic groups such as carboxylate and sulfonate.

BEST MODE FOR CARRYING OUT THE INVENTION

This invention is directed to filter media, particularly filter sheets, comprising a microfibrous, polymeric filter sheet comprised of a normally hydrophobic, microfibrous, polymeric web, wherein the surfaces of the microfibers making up the web are coated with a cured, precipitated, cationic, thermo-set binder resin or polymer. The filter sheet is further characterized by being hydrophilic and having a positive zeta potential.

The subject invention is also directed to the process for preparing such filter sheets and their use in filtration applications. The general method of preparing these filter sheets comprises four steps:

(1) applying a first solution or dispersion of a precipitating agent to a hydrophobic web comprised of polymeric microfibers to at least partially wet the web with this first solution;

(2) applying a second solution of a water-soluble, non-colloidal, cationic, thermosetting binder resin or polymer to the wetted web of step (1) above to form a web wetted with a mixture of the first solution or dispersion and the second solution;

(3) working the wetted web or step (2) above to mix the first solution or dispersion and the second solution, thereby facilitating the precipitation of the binder resin or polymer and the distribution in a uniform manner of the precipitated binder resin or polymer as a coating on the surfaces of the microfibers making up the worked web; and (4) drying the coated web of step (3) above and curing the precipitated binder resin or polymer coating to form the desired filter sheet.

As discussed hereinafter, variations in these four basic processing steps, as well as certain additional processing steps, may be utilized in practicing the process of this invention.

SUITABLE POLYMERS OR BINDER RESINS

The polymers or binder resins useful in preparing the filter sheets of the subject invention are the water-soluble, non-colloidal, cationic, thermo-setting polymers or binder resins. Many such polymers or binder resin materials are readily available from commercial manufacturers in various forms and have found extensive use in paper manufacture as wet strength additives. The general characteristics and uses of these materials are described in, e.g., *Amino Resins*, J. J. Blair, Rheinhold Publishing Company, New York, 1959; *Wet Strength In Paper And Paper Board*, Tappi Monograph Series Number 29, 1965; *Polymeric Amines And Ammonium Salts*, E. J. Goethals, Pergamon Press, New York, 1980. The epoxide-based water-soluble resins are preferred. Suitable epoxide-based water-soluble, cationic, thermosetting polymers commercially available include both polyamido/polyaminoepichlorohydrin resins and polyamine-epichlorohydrin resins.

The binder resins used in this invention must meet several requirements. They must have the ability, while in the uncured state, to form true solutions in water. In this regard, the class of polymers or binder resins useful in this invention are, as described above, water-soluble and non-colloidal. By this is meant that the solution of the polymer or binder resin is applied to the web in a non-colloidal state. It does not mean that the polymer or binder resin is incapable of forming a colloid under appropriate conditions, only that this is an undesirable form of the polymer or binder resin for purposes of this invention.

A second requirement is that the polymer or binder resin must be capable of being cured into the cross-linked state by a simple conversion process involving no more than time, temperature and, optionally, a catalyst.

Still another requirement of the binder resins of this invention is relative insensitivity to water swelling. Water swelling polymers lose mechanical strength as they swell. Crosslinking to a polymer reduces susceptibility to swelling and the mechanical integrity of formed structure containing the polymer is correspondingly enhanced.

A desired characteristic of the binder resins useful in this invention is the presence of a high proportion of cationic charges. Additionally, the cationic charges preferably should not simply rely on protonation. Rather, the charges should stem from quaternized ammonium groups whose cationicity is independent of pH.

Particularly preferred water-soluble, non-colloidal, cationic, thermosetting polymers or binder resins are those containing a substantial number of quaternary ammonium groups, derived from any suitable aliphatic amine which has been fully quaternized.

Representative water-soluble, non-colloidal, cationic, thermosetting polymers or binder resins which may be used to prepare the filter sheets of this invention include those described in U.S. Pat. Nos. 2,926,154, 3,332,901, 3,224,986 and 3,855,158, the disclosures of which are incorporated herein by reference. Commercially available water-soluble, non-colloidal, cationic, thermosetting binder resins or polymers of the polyamido/-polyamino-epichlorohydrin class, which are preferred for purposes of this invention, are Kymene ® 557 and the Polycup ® series of resins manufactured by Hercules Incorporated.

Especially preferred water-soluble, non-colloidal, cationic, thermosetting resins are the polyamine-epichlorohydrin resins which contain quaternary ammonium groups. Resins of this type are made by reacting polyamines with epichlorohydrin and differ from the polyamido/polyamino-epichlorohydrin resins in several respects. They do not contain amide linkages in their composition and, contrary to commercial polyamido/polyamino-epichlorohydrins, derive a substantial degree of their cationicity from the presence of quaternary ammonium groups. Commercial compositions of this type are prepared by reacting epichlorohydrin with condensation products of polyalkylene polyamides and ethylene dichloride. Compositions of this type are disclosed in U.S. Pat. No. 3,855,158 and are exemplified by Santo-res ® 31, a product of Monsanto Inc.

Another form of this particularly preferred type of binder resin is prepared by the reaction of epichlorohydrin with polydiallyl methyl amine to produce an epoxide functional quaternary ammonium resin. Compositions of this kind are disclosed in U.S. Pat. No. 3,700,623 and are exemplified by Resin R4308, a product of Hercules Incorporated. The disclosures of U.S. Pat. Nos. 3,855,158 and 3,700,623 are incorporated herein by reference.

Both these preferred classes of resins are epoxy functional, cationic, thermosetting classes which derive substantial cationicity from quaternary ammonium groups and provide positive zeta potential in alkaline pH.

Many of the polymers or binder resins useful in the subject invention require activation. For the purpose of providing extended shelf life or storage stability to these resins, the epoxide groups are chemically inactivated to prevent premature cross-linking of these resins. Thus, prior to the use of these resins for purposes of the present invention, the resins are activated into the reactive, thermosetting state by regeneration of the epoxide groups. Typically, activation entails adding sufficient aqueous caustic to a solution of the inactive resin to chemically convert the inactive chlorohydrin form to the crosslinking epoxide forms. The parts by weight of aqueous caustic per parts by weight of resin vary with the product and are specified by the manufacturer. The activation process is efficient and complete activation is generally achieved in about 30 minutes, following which the resin solution is ready for use.

PRECIPITATING AGENTS

A variety of precipitating agents are suitable in the practice of this invention. As a first requirement or limitation on the selection of appropriate precipitating agents, the material must be water-soluble or water dispersible and have the ability to precipitate the cationic binder resin from aqueous solution. Synthetic water-soluble or dispersible precipitating agents which are derived from natural or synthetic polymers are preferred. These types of agents are available from many commercial manufacturers and their properties and compositions are described in, for example, *Index Of Commercial Flocculants*, H. A. Hamza and J. L. Picard, 1974 Canmet Report 77-78, Canada Centre For Mineral And Energy Technology, Canada, 1975; and *Ind. Min. J.* (Special Issue), R. D. Booth, J. E. Carpenter and H. Hartjens, 335, 1957. Precipitation of the cationic binder resin onto the microfiber surfaces of the polymeric web by the addition of high-molecular weight polymers containing anionic charges has been found especially effective.

It is believed that the combination of a solution of a cationic binder resin with a water-soluble or dispersible anionic percipitate under the conditions described herein, causes the formation of a precipitated form of the cationic binder resin which adheres efficiently to the surfaces of the microfibers in the microfibrous, polymeric web. The interaction of the binder resin or polymer with the precipitating agent may result in precipitation of the precipitating agent together with binder resin. It should, therefore, be understood that the coating composition of the polymeric web may contain a proportion of the precipitating agent.

It is also believed that the remarkable ability to control the quantity of cationic binder resin deposited on the polymeric web by precipitation in the manner described herein may result, in part, from favorable zeta potential interactions between the cationic binder resin precipitate and the surfaces of the microfibers in the polymeric web. Such interactions are known to be complex and various other mechanisms, such as electrostatic bonding, hydrogen bonding or other physicochemical interactions, may be responsible in whole or in part for the extremely desirable results obtained. Whatever the detailed interactions may be, it has been found that the combination of polymeric anionic precipitating agents with water-soluble, non-colloidal, thermosetting cationic binder resins or polymers within a normally hydrophobic, microfibrous, polymeric web leads to the efficient coating of the surface of the microfibers in the web by the cationic binder resin. The small quantities of binder resin or polymer required to significantly improve the mechanical strength of such webs is also believed to be a reflection of the efficiency and substantial uniformity with which the surfaces of the webs are coated by the method described.

Since the anionic precipitating agents preferably used in this invention contain carboxyl or other ionizable acidic groups, their precipitating efficiency is a function of pH. Accordingly, the preparation of the binder resin or polymer coated polymeric webs used to prepare the filter sheets of this invention is most effectively carried out at pH conditions wherein the anionic groups are substantially completely ionized and provide the highest precipitation efficiency, that is, preferably under alkaline conditions.

The preferred precipitating agents may be selected from a group of synthetic, water-soluble or dispersible polymers containing anionic groups such as carboxylate or sulfonate. The carboxylate-containing polymers, such as acrylic acid copolymers, are especially preferred due to their efficiency, wide availability and low cost. Suitable precipitating agents for the purpose of this invention include anionics such as the Hercoflocs ® manufactured by Hercules Incorporated, the Puriflocs ® manufactured by Dow Chemical Corporation and the Nalcolyte ® series of anionic flocculants manufactured by Nalco Chemical Company. Suitable commercial precipitating agents include Nalcolyte ® 7763, 7766 and 7173, Product 18,127-7 (Aldrich Chemical Company) and Carboset 531 (B. F. Goodrich Company). Nalcolyte ® 7766 and 7173 are high molecular weight (greater than one million) copolymers of acrylamide and sodium acrylate. Nalcolyte ® 7763 is a copolymer having a molecular weight of from about 5 to 10 million prepared by reacting about 35 percent acrylic acid and about 65 percent acrylamide. The general structures of these materials are set out in U.S. Pat. Nos. 3,549,527, 3,617,542 and 3,673,083. They are ionic flocculating agents with the extent of ionicity determined by the relative proportion of sodium acrylate in the polymer. They are prepared by the controlled hydrolysis of polyacrylamide to polyacrylamide-coacrylate and also by the direct copolymerization of acrylamide with sodium acrylate. Product 18,127-7 is a polyacrylamide with a molecular weight of 5 to 6 million. The particularly preferred precipitating agent, Carboset 531, is a water-soluble, self-catalyzed, thermosetting, acrylic resin with a molecular weight of about 1 million. It is believed to contain N-methylol acrylamide groups and acrylic acid groups through which the crosslinking occurs.

MICROFIBROUS, POLYMERIC WEBS

The base webs useful for preparing the filter sheets of the subject invention are comprised of polymeric microfibers. As used herein, "microfibers" or "microfibrous" refers to fibers typically having diameters of from about 0.5 to about 20 micrometers, preferably from about 1.0 to about 10 micrometers. They may typically vary in length from relatively short staple-like microfibers of about 0.5 inches or less up to substantially continuous filaments several feet or more in length.

The webs formed with these polymeric microfibers can be formed in a variety of ways well known in the industry. A preferred technique is in "The Manufacture Of Superfine Organic Fibers", V. A. White, U.S. Department of Commerce, Naval Research Laboratory, Publication PB111437 (1954).

The microfibrous, polymeric webs useful for preparing the filter sheets of this invention are preferably nonwoven and prepared from melt-spun polymeric microfibers such as polyolefins, e.g., polypropylene and polyethylene; polyesters, e.g., polybutylene terephthalate and polyethylene terephthalate; and polyamides, e.g., polyhexamethylene adipamide (nylon 66), polyhexamethylene sebacamide (nylon 610); nylon 11, prepared from 11-amino-nonanoic acid; and homopolymers of poly-e-caprolactam (nylon 6). Other polymers which can be formed into microfibers and which form hydrophobic microfibrous webs, particularly those which can be melt-spun to form microfibers of from about 0.5 to about 20 micrometers, may also be used. Webs comprised of mixtures of different polymeric microfibers may also be used. Preferred webs are the hydrophobic, microfibrous webs available commercially from Pall Corporation under the trademark HDC ®. These webs are comprised of polypropylene microfibers, typically having microfiber diameters of from about 1.0 to about 10 micrometers, have a high dirt capacity, are available in absolute pore ratings of from about 0.6 to about 70 micrometers at weights ranging from 1 to 20 grams per square foot and tensile strengths of from 1.5 to 8.5 pounds per inch.

The microporous webs formed from microfibers of these polymers have in common that they are hydrophobic prior to conversion to a hydrophilic form by the process of this invention and have a negative zeta potential in alkaline media. As used herein, the term "hydrophobic" means not wetted by water, as evidenced by a high angle of contact at the watermicrofiber or microfibrous web interface.

Also as used herein, the term "hydrophilic" means readily wetted by water, which is visually observable by the rapid spreading of a drop of water placed in contact with the microfiber or the microfibrous web.

The weights of the hydrophobic, microporous, polymeric webs useful in forming the filter sheets of this invention are typically in the range of about 0.5 to about 20 grams per square foot, preferably about 1 to about 10 grams per square foot. Typically, the hydrophobic, microporous webs have absolute pore ratings of from about 0.5 to about 80 micrometers, preferably from aboud 0.6 to about 10 micrometers.

METHOD OF PREPARATION

The process or method of preparing the filter sheets of the present invention basically involves the following four steps:

(1) applying a first treating solution or dispersion of a precipitating agent to a hydrophobic web comprised of polymeric microfibers to at least partially wet the web with this first solution;

(2) applying a second treating solution of a water-soluble, non-colloidal, cationic, thermosetting binder resin or polymer to the wetted web of step (1) above to form a web wetted with a mixture of the first solution or dispersion and the second solution;

(3) working the wetted web of step (2) above to mix the first solution or dispersion and the second solution, thereby facilitating the precipitation of the binder resin or polymer and the distribution thereof as a coating on the surfaces of the microfibers making up the worked web; and (4) drying the coated web of step (3) above and curing the precipitated binder resin or polymer coating to provide a hydrophilic, microfibrous, polymeric filter sheet with a positive zeta potential and which is further characterized by the surfaces of the microfibers therein being coated with a cured, precipitated, thermoset, cationic binder resin or polymer.

Variations in these four basic steps, as well as certain additional processing steps, may be utilized in practicing the process of this invention. For example, steps (1) and (2) above can be reversed, albeit the preferred order of application is as set out above.

As another and less preferred alternative, the first and second treating solutions, as described in steps (1) and (2) above, can be applied substantially simultaneously by, for example, spraying them through separate nozzles onto the surface of the hydrophobic web. It is necessary, however, in practicing the process or method of this invention, that substantially all of the mixing of the first and second treating solutions occurs while the solutions are in contact with the web so that the precipitation of the binder resin or polymer and its distribution on the web occurs in a substantially uniform manner.

Additionally, it may be desirable in certain instances to use prewetting solutions containing a wetting agent such as a surfactant, or a lower alcohol, e.g., tertiary butyl alcohol, n-butyl alcohol, ethanol, or isopropanol, in aqueous solution to prewet the hydrophobic webs, followed by water washing to remove at least the major portion of the wetting agent from the web, preferably as completely as possible, while maintaining the web in a water wetted form, and then applying the first and second treating solutions as described above or in reverse order. (Herein, the terms "solution" or "treating solution" are sometimes used in describing processing under steps (1) and (2) above.) It should be understood that when the precipitating agent containing composition is being referred to it may be present as either a solution or a dispersion.)

With some hydrophobic, microfibrous, polymeric webs, e.g., nylon 66 and polybutylene terephthalate, the prewetting step can be eliminated by including in the first treating solution a wetting agent, such as a lower alcohol, to lower the surface tension of the treating solution, thereby facilitating the wetting of the web. The level of alcohol required to reduce the surface tension of the treating solution the requisite amount can be determined by trial and error. The alcohol used and the amount present in the treating solution, of course, must be at a sufficiently low level to not interfere with the coating process.

Additionally, it may be desirable, with some carboxylate precipitating agents, to convert some of the carboxylic acid groups therein to their salt form by neutralization with inorganic bases, e.g., sodium hydroxide, or organic bases, e.g., diethanolamine or triethanol amine. This treatment improves the solubility of the precipitating agent and, in some instances, improves the wetting characteristics of the solution or dispersion of the precipitating agent in the treatment of the hydrophobic web.

When the binder resin or polymer is used as the first solution, i.e., when it is applied to the web first in step (1) above, a wetting agent may also be desirable to improve the wetting characteristics of the binder resin or polymer solution, thereby eliminating the prewetting step with some hydrophobic, microporous, polymeric webs, e.g., nylon 66 and polybutylene terephthalate.

Preferably, the hydrophobic web is fully wetted, i.e., saturated, in step (1) above, i.e., with the first solution added, whether that be a solution of the precipitating agent or the solution of the binder resin or polymer. Prior to the application of the second solution to the web, any excess of the first solution may be removed, e.g., by mechanical wiping using a wiper blade or the like, padding etcetera. Preferably, prior to the application of the second solution to the web, a sufficient portion of the first solution is removed so that the web is not fully wetted, i.e., saturated, with the first solution when the second solution is applied.

After the second solution has been applied and the web preferably fully wetted with a mixture of the first and second solutions, it is necessary to work the wetted web to mix the first solution and second solution, thereby facilitating the precipitation of the binder resin or polymer and the distribution thereof as a coating on the surfaces of the microfibers making up the worked web. This working can be carried out by a variety of techniques, including mechanical agitation, the action of tensioned wiper blades or subjecting the web to pressure between two rollers or a roller and a flat surface, or by contacting one surface of the web with a counter rotating roller.

The preferred method of working the wetted web is by contacting it with a roller rotating counter to the direction the web is moving as the web moves past this roller. In practice, using this technique, the first solution is preferably applied to a rotating transfer roller in the form of a film which is applied to and absorbed by the web as the transfer roller, which is in contact with the web, rotates over the top surface of the web which is being drawn past the roller. Preferably, the web is then subjected to the action of a wiper blade to remove excess solution from the web to aid absorption of the second treating solution, following which the second solution is applied to the web by means of a second transfer roller to which the second solution has been applied in the form of a film. The second transfer roller is preferably the roller power driven counter to the direction of the web and, preferably, at about the linear velocity of the web to aid the mixing, precipitation and distribution as described above.

In this preferred processing technique, the web is threaded through a series of at least three horizontally aligned rollers in an under/over/under configuration with the first roller applying the first solution to the surface of the web as the web passes under it; the middle roller over which the web passes operating in conjunction with a wiper blade to remove any excess of the first solution following which the web passes under a third power driven roller rotating counter to the web direction (the second transfer roller), which applies the second solution to the web. The third roller also mixes the first and second solutions by working the fully wetted web, thereby precipitating the binder resin or polymer and coating the surfaces of the microfibers making up the web.

Other techniques for applying the first and second solutions may also be used, including the use of a doctor blade to form films of the two solutions on separate surfaces, following which the web is sequentially contacted with the individual films of the two solutions.

After the web has been worked and the binder resin or polymer has been precipitated onto the surfaces of the microfibers of the worked web to form a coating, preferably of substantially uniform thickness, the web is dried to remove volatile components, primarily water, and cured to convert the binder resin or polymer to the crosslinked state.

The term "drying" is used herein to primarily describe the phenomenon by which volatile materials, e.g., water, are removed from the system. It should be understood, however, that the precipitated binder resin or polymer coating the surfaces of the microfibers making up the base web is also cured to convert the binder resin or polymer into a crosslinked, mechanically strong and water-insoluble form providing enhanced bonding between the microfibers making up the base web, i.e., the normally hydrophobic web, of the filter sheets of this invention. The two phenomena may be part of a continuum with curing occurring as the drying process is carried out. Curing is accelerated by the use of elevated temperatures and by the removal of water from the system. Drying and curing may also be carried out at ambient temperatures over an extended period, dependent upon the particular combination of binder resin or polymer and precipitating agent. Drying and curing are more expeditiously effected by the use of elevated temperatures between 50 and 150 degrees C. for as much as several days to as little as several minutes. Cure times of from about 5 to 60 minutes in combination with a curing temperature of about 75 to 130 degrees C. are generally preferred.

Preferably the method of this invention is carried out in a continuous manner. However, if an extended dry and cure time is used, it may be desirable to carry out the first three steps, as set out above, in a continuous fashion and carry out the drying and curing step in a separate, but preferably continuous step, off-line, in effect, from (1) the first three processing steps, as well as, of course, (2) any pretreating step, e.g., prewetting and washing prior to application of the first treating solution in the first step described above, or (3) any intermediate step, e.g., removing a portion of the first treating solution prior to applying the second treating solution in step (2).

CONCENTRATIONS OF THE VARIOUS CONSTITUENTS

The concentration of the precipitating agent in the first treating solution or dispersion is typically in the range of from about 2.5 to about 7.5 percent. (All parts and percents herein are by weight based on the weight of the total composition of the particular solution, dispersion or other entity under consideration unless otherwise specified.) Preferably, the precipitating agent will be present in the first solution or dispersion in an amount of from about 3 to 6 percent. The term "first solution or dispersion" is used here to be consistent with the wording of the basic four step process described above. It should be understood that while referred to as the first treating solution or dispersion, it may in fact be applied as the second applied treating solution when the order of application of the treating solutions is reversed.

The concentration of the water-soluble, non-colloidal, cationic, thermosetting binder resin or polymer in the second treating solution may typically vary from less than 0.1 percent to as high as 20 percent in the practice of the process of this invention. More typically, the range will be from about 1 to about 10 percent. In the case of the preferred binder resin or polymer, Resin R4308, weight concentrations of from about 0.1 to about 10 percent are preferred, more preferably from about 1 to about 5 percent. Similar to the explanation provided above concerning the "first solution", the "second solution" of the binder resin or polymer may in fact be the first applied treating solution.

The cationic binder resin or polymer is preferably applied to the polymeric web as an aqueous solution in an amount such that the total weight of the cationic binder resin or polymer solids added, based on the dry weight of the base hydrophobic web prior to any treatment, ranges from about 1 percent to as high as about 30 percent, preferably from about 5 to about 15 percent. It should be understood, as discussed elsewhere herein, that the precipitating agent may, in the course of precipitating the binder resin or polymer, be chemically bound and/or physically intermixed with the binder resin or polymer and thereby become a part of the coating on the microfibers. The percentages set out immediately above refer only to the binder resin applied to the polymeric web as an aqueous solution. The amount of binder resin or polymer deposited on the microfiber surfaces of the web will preferably approach the amount applied to the web, but some may be lost in processing.

The quantity of precipitating agent required to precipitate the cationic binder resin or polymer onto the surfaces of the microfibers making up the hydrophobic web may vary from as little as about 25 percent to as high as about 100 percent (dry weight of precipitant based on the dry weight of the cationic binder resin or polymer). The proportion will vary with the specific nature of the cationic thermosetting binder resin or polymer and the precipitating agent combination. Preferably, the relative weight proportion of the precipitating agent should be maintained at levels no greater than that of the cationic thermosetting binder resin or polymer. It should be understood that the relative weight proportions of the precipitating agent and the binder resin or polymer referred to herein are the amounts present in the web just prior to the working of the web to facilitate mixing of these two compounds and precipitation of the binder resin or polymer onto the microfiber surfaces. An excess quantity of the first solution, whether that is (1) the precipitating agent solution or (2) the binder resin or polymer solution, may be applied initially to insure the preferred complete wetting of the web following which a portion may be removed.

For the preparation of hydrophilic, microfibrous, polymer filter sheets with the preferred cationic binder resin or polymer, R4308, and the preferred precipitating agent, Carboset 531, the preferred weight ratio of binder resin to precipitating agent is in the range of from about 4:1 to about 1:1, more preferably from about 2:1 to about 1:1.

PRODUCTS OF THIS INVENTION

The hydrophilic, microfibrous, polymeric filter sheets prepared by the process of this invention will typically have dry tensile strengths ranging from about 2 to about 15 pounds per inch. They can, of course, be used in the form of flat planar sheets. They can also be mechanically worked into pleated or corrugated forms (accordion forms) by methods well known to those skilled in the art and incorporated into filter element structures, such as filter cartridges, of the type well known in the industry.

The hydrophilic, microfibrous, polymeric filter sheets of this invention are further characterized by having positive zeta potentials in both acid and alkaline media, typically over a broad pH range of from about 3 to about 10. The filter sheets are hydrophilic, as defined above, and, compared with the hydrophobic, microfibrous, polymeric webs from which they are formed, have substantially improved aqueous flow rates at the same applied pressure or, in the alternative, lower differential pressure at the same flow rate.

Typically, the filter sheets of the present invention have absolute pore ratings ranging from about 0.5 to about 80 micrometers, preferably from about 0.5 to about 10 micrometers, and removal ratings for negatively charged particles ranging down to as low as about 0.1 micrometer or even finer. In comparison with the base hydrophobic, microfibrous, polymeric webs from which they are formed, the tensile strengths are typically increased by a factor of from 25 to as much as 100 percent. That is, the corresponding base webs will typically have dry tensile strengths ranging from 1.5 to 8.5 pounds per inch compared with the 2 to about 15 pounds per inch for the hydrophilic, microfibrous, polymeric filter sheets of the subject invention. The improved tensile strengths result from the coating of the surfaces of the microfibers of the base web with the cured, precipitated, cationic, thermoset binder resin or polymer. The resulting hydrophilic, microporous filter sheet typically contains from about 1 to about 30 percent of the cured, precipitated, cationic, thermoset binder resin or polymer, preferably from about 5 to 15 percent, based on the dry weight of the base hydrophobic web prior to any treatment. As noted above, the precipitating agent may also form a part of the coating on the microfibers. The percentages set out immediately above refer only to the precipitated binder resin or polymer. It should be understood that while preferably all of the binder resin or polymer applied to the web is precipitated onto the surfaces of the microfibers and incorporated thereby into the web, a portion may be lost during processing.

The conversion of hydrophobic, microporous, polymeric webs having negative zeta potentials in alkaline media to hydrophilic, microfibrous, polymeric filter sheets having (i) positive zeta potentials with concomitant enhanced particle removal efficiencies for negatively charged particles, (ii) enhanced flow rates at a given applied pressure and (iii) enhanced mechanical strength are substantial improvements in the properties of this type of filtering media. These characteristics are illustrated by the following examples.

METHOD OF TESTING THE FILTER SHEETS OF THE FOLLOWING EXAMPLES

The properties of the microfibrous filter sheets of the following examples were evaluated by a variety of test methods, as described below:

(a) Tensile Strength:

Tensile strength was measured on an Instron Universal Testing Instrument Model 1130, according to the ASTM Method D882.

(b) Zeta Potential:

The zeta potentials of the microfibrous filter sheets were calculated from measurements of the streaming potentials generated by flow of a 0.001 weight percent solution of KCl in distilled water through several layers of the filter sheet secured in a filter sheet holder. Zeta potential is a measure of the net immobile electrostatic charge on a filter sheet surface exposed to a fluid. It is related to the streaming potential generated when that fluid flows through the filter sheet by the following formula (J. T. Davis et al, *Interfacial Phenomena*, Academic Press, New York, 1963):

$$\text{Zeta Potential (mV)} = \frac{4\pi\eta}{D} \cdot \frac{E_s \lambda}{P}$$

wherein $\eta$ is the viscosity of the flowing solution, $D$ is the dielectric constant of the solution, $\lambda$ is its conductivity, $E_s$ is the streaming potential, and $P$ is the pressure drop across the filter sheet during the period of flow. In the following examples, the quantity $$\frac{4\pi\eta}{D}$$

is constant, having the value $2.052 \times 10^{-2}$, making the zeta potential equal to:

$$\text{Zeta Potential (mV)} = \frac{2.052 \times 10^{-2} \cdot E_s(\text{Volt}) \cdot \lambda(\text{umho/cm})}{P}$$

(c) OSU F-2 Filter Performance Test (Aqueous Particulate Removal Efficiency Test):

A procedure for determining filter removal ratings in aqueous service is the OSU F-2 filter performance test which has gained wide acceptance in various industries. The apparatus used is an automatic particle counter, Model PC-320, available from Hiac-Royco Instruments of Menlo Park, Calif. The device has a CMB-60 detector upstream, a CM-60 detector downstream, and allows the rapid challenge of test membranes with an aqueous suspension of silicious test dust in the particle diameter range of from 0.1 to 40 micrometers. The apparatus has two sets of six channel particle counters which can be set to any six preselected particle sizes in the range of from 1 to 40 micrometers in diameter and automatically record particle concentrations in the incident flow and effluent flow from the filter. The apparatus also automatically records the ratio known as beta ($\beta$), which is the ratio of the number of incident particles to the number of effluent particles at each of the six particle diameters selected. Beta is related to particle removal efficiency, expressed as percent removal, as follows:

$$\% \text{ removal} = \frac{\beta - 1}{\beta} \times 100.$$

(d) Latex Particle Removal:

Monodisperse suspensions of polystyrene latex with well-characterized particle sizes (available from Dow Diagnostics Inc.) were prepared in approximate 0.1 percent by weight solutions in deionized water containing 0.1 percent Triton X-100 (an adduct of nonyl phenol with about 10 moles of ethylene oxide). Latex suspensions were pumped through the test filter sheets positioned in a disc holder 47 millimeters in diameter and having an effective filtration area of 0.01 square feet (9.29 cm$^2$) using a Sage Instrument Model 341 syringe pump at a rate of 2 milliliters per minute. The effluent was passed through an optical flow cell in a light scattering photometer (Model 2000D, available from Phoenix Precision Instrument Inc.). The scattering signal from a beam of 537 nm light, measured at 90 degrees, was converted to latex bead concentration by means of an empirically determined concentration-scattering intensity correlation for each latex size. Latex bead capacities were derived from measured efficiencies and total volume of latex bead challenge by the following formula:

$$\frac{\text{concentration of input (0.1\%)}}{\text{concentration of effluent}} = \beta$$

$$\% \text{ removal efficiency} = \frac{\beta - 1}{\beta} \times 100.$$

(e) Water Flow Test:

The rate of water passing through a filter sheet at a specified applied pressure was determined as follows. A 90 mm diameter circular disc of the filter sheet to be tested was placed in a holder having an effective test area of 0.069 square feet. Prefiltered water was then passed through the filter sheet in the holder and the desired pressure differential across the filter sheet was obtained by adjusting the water flow rate. The flow rate of water through the test holder was then measured and converted into units of liters per minute per square foot of filter area. The pressure differential across the filter sheet was also measured as pounds per square inch difference (psid).

(f) Bubble Point Test:

The capillary displacement pressure of a liquid from a pore is proportional to the surface tension of the liquid. Therefore, a high surface tension liquid, such as water, will have a higher bubble point pressure than a low surface tension liquid, such as alcohol, for a given pore size. Accordingly, a correlation curve between bubble point pressure and average pore size can be generated for any given wetting liquid.

The filter sheet to be tested was immersed in deionized water for about five minutes. Hydrophilic filter sheets are readily wetted by the water while hydrophobic filter sheets are not. After immersing in water, the filter sheet was placed in a holder having an effective test area of 0.069 square feet. Air pressure was then applied across the filter sheet while total air flow through the filter sheet was measured. For hydrophilic webs, the air flow is limited to very low diffusive flow through the wetted porous fiber network. For hydrophobic webs, air readily passes through the filter sheet at high flow rates since the pores of the filter sheet are not wetted by and filled with water.

When a water wettable filter sheet, i.e., hydrophilic filter sheet, is immersed in water, all the pores are wetted and become filled by water. When such a filter sheet is subjected to the procedure as described above, air flow through the filter sheet is diffusive at applied pressures below the capillary displacement pressure. As the capillary displacement pressure is attained, the water is rapidly expelled from the pores and the flow rate of air through the filter sheet rises dramatically. This is the bubble point or capillary displacement pressure (measured in inches of mercury) for the filter sheet and is inversely proportional to the average pore diameter of the filter sheet. The applied pressure which yields a flow of 1500 cc/minute per square foot of filter sheet area through the filter sheet is the 1500 cc bubble point of the filter sheet. The untreated hydrophobic webs are not wettable with water. However, they can be bubble point tested by wetting them with a solution of a low surface tension wetting solution, such as 95 percent ethanol in water solution, and then testing them as set out above.

GENERAL METHOD FOR PREPARING THE FILTER SHEETS OF THE FOLLOWING EXAMPLES 1-3

A hydrophobic web of substantially continuous melt-spun polypropylene microfibers having a mean fiber diameter of about 1.9 micrometers (the web had a weight of about 4 grams per square foot) was immersed in a 7 percent solution of n-butyl alcohol in deionized water to fully wet the web. Deionized water was then passed through the web to a total volume of about 0.5 liter per square foot to rinse the alcohol from the web while maintaining the web in its wetted form. A first aqueous solution, containing 5 percent of a precipitating agent, Carboset 531, and 1.2 percent diethanolamine was then applied to the wetted web with a transfer roller at a rate of about 12 milliliters per square foot of web.

The web was then subjected to the action of a wiper blade to remove excess first solution from the web following which a second solution containing 5 percent of a binder resin or polymer, Resin R4308, in deionized water was applied to the web at a rate of about 12 milliliters per square foot of web by means of a second transfer roller. This roller was power driven counter to the direction of the web at about the same linear velocity as the web to mix the first and second solutions and facilitate the precipitation and distribution of the binder resin or polymer as a coating on the surfaces of the microfibers of the polypropylene web.

The resulting coated web was then dried and cured using infrared heating to form a hydrophilic filter sheet of polypropylene microfibers, the surfaces of which were coated with a cured, precipitated, thermoset, cationic binder resin or polymer.

Example 1

A web of melt-spun polypropylene microfibers having a bubble point pressure of 2.0 inches of mercury (wetted with a 9.5 percent ethanol in water solution) corresponding to an average pore diameter of about 9 micrometers, as determined by the Bubble Point Test described above was treated by the General Method described above. Following the application of the first solution of the precipitating agent, the 5 percent aqueous solution of the binder resin or polymer was applied with a transfer roller counter-driven at about 60 RPM while the web was moving at about 11 feet per minute. The resulting coated web was then dried and cured for 5 minutes at 120 degrees C..

The filter sheet of Example 1 was tested for the properties set out in the first column of Table I below. For comparison, a Control, the same polypropylene web used in preparing the filter sheet of Example 1 but untreated, was tested for the same properties. The results are set out in Table I.

TABLE I

| TEST | FILTER SHEET OF EXAMPLE 1 | CONTROL (Untreated) |
|---|---|---|
| Zeta Potential | +7.54 millivolts at a pH = 7.15 | −28 millivolts at a pH = 7.15 |
| Bubble Point (water wetted) | 5.7 inches mercury | not testable with water since hydrophobic |
| Water Flow Rate (at 2 psi, differential pressure) | 62.8 liters per min. per sq. ft. | 13.7 liters per min. per sq. ft. |
| Percent Removal Efficiency for 1.74 Micrometer Latex Beads | 99.98% | 0% |
| Tensile Strength | 6.73 pounds per inch | 4.42 pounds per inch |

Example 2

A web of melt-spun polypropylene microfibers having a bubble point pressure of 7.8 inches of mercury (wetted with a 95 percent ethanol in water solution) corresponding to an average pore diameter of about 5 micrometers was treated by the General Method described above. The web was subjected to the same treatment as described in Example 1 except that the web was dried and cured for 20 minutes at 175 degrees F.. The resulting filter sheet and a corresponding Control (the same polypropylene web used in preparing the filter sheet of Example 1 but untreated) were then tested with the results set out in Table II below.

TABLE II

| PROPERTY | FILTER SHEET OF EXAMPLE 2 | CONTROL |
|---|---|---|
| Zeta Potential at pH = 7.9 | +4.8 mv | −28 mv |
| Bubble Point (water wetted) | 19 inches Hg | not testable with water since hydrophobic |
| Water Flow (at 5 psi, differential pressure) | 8.8 liters per min. per sq. ft. | 1.1 liters per min. per sq. ft. |
| Removal efficiency for 0.8 micrometer latex beads | 99.9997% | 50% |

Example 3

The filter sheets of Examples 1 and 2 were converted into pleated filter elements by methods well known in the art. The efficiency of these elements for removing silicious particles from aqueous suspensions by the OSU F-2 Filter Performance Test was then determined. For comparative purposes, pleated Control filter elements were prepared from the corresponding untreated polypropylene webs used to prepare the filter sheets of Examples 1 and 2 respectively and similarly tested. The results are set out in Table III below.

TABLE III

| Element of Example | Percent Removal Efficiency At Indicated Particle Diameter In Micrometers | | |
|---|---|---|---|
| | 1.0 micrometers | 2.0 micrometers | 3.0 micrometers |
| 1 | 99.7 | 99.98 | 99.999 |
| Control | 10 | 90 | 95 |
| 2 | 99.99 | 99.998 | 99.994 |
| Control | 99.7 | 99.7 | Not Done |

Example 4

A web of polypropylene microfibers identical to that used in Example 1 was treated by the General Method described above except that the cationic thermosetting binder resin or polymer was Santo-rez ® 31. Following application of the 5 percent Carboset 531 solution, a 5 percent aqueous solution of Santo-rez ® 31 was applied with a transfer roller counter driven at about 60 RPM while the web was moving at about 11 feet per minute. The treated web was then dried and cured for 5 minutes at 120 degrees C..

The resulting filter sheet was tested for the properties itemized in the first column in Table IV below. For comparison a Control, the same polypropylene web used in preparing the filter sheet of this Example but untreated, was tested for the same properties. The results are set out in Table IV.

TABLE IV

| TEST | FILTER SHEET OF EXAMPLE | CONTROL (Untreated) |
|---|---|---|
| Zeta Potential | +2.77 millivolts at pH = 7.5 | −28 millivolts at pH = 7.15 |
| Bubble Point (water wetted) | 5.5 inches mercury | not testable with water since hydrophobic |
| Tensile Strength | 5.43 pounds per inch | 4.43 pound per inch |
| Percent Removal Efficiency for 1.74 Micrometer Latex Bead (Latex Particle Removal Test) | 99.83% | 0% |

GENERAL METHOD FOR PREPARING THE FILTER SHEETS OF EXAMPLES 5 AND 6

A first solution containing 5 parts of a precipitating agent, Carboset 531, 1.2 parts diethanolamine, 20 parts tertiary butyl alcohol and 73.8 parts deionized water was spread as a film about 0.01 inches thick on a glass plate using a doctor blade. A hydrophobic, polymeric, microfibrous web was then placed in contact with this film.

In a similar manner a solution containing 4 parts of a binder resin or polymer, Resin R4308, 20 parts tertiary butyl alcohol and 76 parts water was formed into a film about 0.01 inches thick on a second glass plate using a doctor blade. The microfibrous web wetted with the film of the first solution from the first glass plate was removed from the first glass plate and contacted with the film of the second solution on the second glass plate. A roller was used to apply moderate pressure to mix the first and second solutions in the web material, precipitate the binder resin, Resin R4308, and coat the microfibers of the web. The treated web was then dried and cured for 1 hour in a convection oven held at 230 degrees F.. Note that while tertiary butyl alcohol was present in the second solution in this General Method, it is optional.

Example 5

A 10 inch by 10 inch section of a nylon 66 microfibrous web with a weight of 3.5 grams per square foot and composed of microfibers with a mean diameter of about 2 micrometers was treated by the General Method described immediately above. As indicated in Table V below, the resulting filter sheet was hydrophilic and had a positive zeta potential in alkaline media. A Control (the base nylon 66 web prior to treatment) was hydrophobic and had a negative zeta potential as also shown in Table V.

TABLE V

| TEST | FILTER SHEET OF EXAMPLE 4 | CONTROL (Untreated) |
|---|---|---|
| Bubble Point (water wetted) | 4.7 inches Hg | not testable with water since hydrophobic |
| Zeta Potential | +2.44 mv at pH = 7.9 | −11.5 mv at pH = 7.9 |

Example 6

A microfibrous web of polybutylene terephthalate microfibers having a mean diameter of about 1.7 micrometers was treated in the same manner as the web in Example 4 and using the same treating solutions. The resulting filter sheet was hydrophilic and had a positive zeta potential in alkaline media as indicated in Table VI below. A Control (the base polybutylene terephthalate web prior to treatment) was hydrophobic and had a negative zeta potential as also shown in Table VI.

TABLE VI

| TEST | FILTER SHEET OF EXAMPLE 5 | CONTROL (Untreated) |
|---|---|---|
| Bubble Point (water wetted) | 4.1 inches Hg | not testable with water since hydrophobic |
| Zeta Potential | +2.81 mv at pH = 7.6 | −78 mv at pH = 7.6 |

INDUSTRIAL APPLICABILITY

Filter elements prepared from filter sheets of this invention are useful as pre-filters, greatly extending the life of very fine filters used downstream of the pre-filter. An area of particular use for such pre-filters is the pharmaceutical industry, e.g., in the preparation of sterile water. Additionally, filters of this invention have greatly reduced fiber and other particulate release characteristics and are, therefore, useful in a variety of pharmaceutical applications where a filtering step is required. Filter elements prepared from the filter sheets of this invention are capable of removing very fine particulates down to molecular dimensions, making these elements particularly useful in the filtering of parenteral fluids. Because of their hydrophilic or water wetting nature, products of this invention deliver high aqueous flow at low differential pressure, making them desirable for use in the clarification of food and beverage products.

The subject invention also has applicability in the filtration of ultra-pure deionized water, such as that used in electronics manufacturing.

Many other potential industrial applications exist which require filter sheets possessing high particulate removal efficiencies and low differential pressure at required flows.

We claim:

1. A process for converting a hydrophobic web comprised of polymeric microfibers to a hydrophilic, microfibrous, polymeric filter sheet exhibiting a positive zeta potential comprising:
   (1) applying a first solution or dispersion of a precipitating agent to said web to at least partially wet said web with said first solution or dispersion;
   (2) applying a second solution of a water-soluble, non-colloidal, cationic, thermosetting binder resin or polymer to the wetted web of step (1) above to form a web wetted with a mixture of said first solution or dispersion and said second solution;
   (3) working the wetted web of step (2) above to mix said first solution or dispersion and said second solution thereby facilitating the precipitation of said binder resin or polymer and the distribution thereof as a coating on the surfaces of the microfibers of the worked web; and
   (4) drying the coated web of step (3) above and curing the precipitated binder resin or polymer to provide a hydrophilic, microfibrous, polymeric filter sheet with a positive zeta potential and which is further characterized by the surfaces of the microfibers therein being coated with a cured, precipitated, thermoset, cationic binder resin or polymer.

2. The process of claim 1 wherein said working of the wetted web of step (2) is carried out by contacting said wetted web with a roller rotating counter to the direction said wetted web is moving as the web moves past said roller.

3. The process of claim 2 wherein steps (1), (2) and (3) are carried out in a continuous manner.

4. The process of claim 3 wherein in step (1) said web is saturated with said first solution or dispersion following which a portion of said first solution or dispersion is removed from said wetted web of step (1) prior to applying said second solution in step (2).

5. The process of claim 1 wherein said drying and said curing in step (4) are carried out at an elevated temperature of from about 50 to about 150 degrees Centigrade for a period of from several minutes to several days.

6. The process of claim 5 wherein said drying and said curing in step (4) are carried out at an elevated temperature of from about 75 to about 130 degrees Centigrade for a period of from about 5 to about 60 minutes.

7. The process of claim 1 wherein said polymeric microfibers of said hydrophobic web are comprised of a polyolefin and said hydrophobic web is prewet with a wetting solution comprising water and a wetting agent prior to step (1) of claim 1.

8. The process of claim 7 wherein said polyolefin is polypropylene.

9. The process of claim 1 wherein said polymeric microfibers of said hydrophobic web are comprised of a polyamide.

10. The process of claim 9 wherein said polyamide is nylon 66.

11. The process of claim 9 wherein said polyamide is nylon 11.

12. The process of claim 1 wherein said polymeric microfibers of said hydrophobic web are comprised of a polyester.

13. The process of claim 12 wherein said polyester is polyethylene terephthalate.

14. The process of claim 12 wherein said polyester is polybutylene terephthalate.

15. The process of claim 1 wherein said hydrophobic web is comprised of microfibers having diameters of from about 0.5 to about 20 micrometers and said hydrophobic web has absolute pore ratings of from about 0.5 to about 80 micrometers.

16. The process of claim 15 wherein said microfibers have diameters of from about 1.0 to about 10 micrometers and said hydrophobic web has an absolute pore rating of from about 0.6 to about 10 micrometers.

17. The process of claim 1 wherein the concentration of said binder resin or polymer in said second solution is in the range of from about 0.1 to about 20 percent.

18. The process of claim 16 wherein the concentration of said binder resin or polymer in said second solution is in the range of from about 0.1 to about 10 percent.

19. The process of claim 18 wherein the concentration of said binder resin or polymer in said second solution is in the range of from about 1 to about 5 percent.

20. The process of claim 17 wherein the concentration of said precipitating agent in said first solution or dispersion is in the range of from about 2.5 to about 7.5 percent.

21. The process of claim 1 wherein said second solution is applied to said wetted web of step (1) in an amount such that the total weight of said binder resin or polymer added to said wetted web of step (1) is from about 1 to about 30 percent based on the dry weight of said hydrophobic web.

22. The process of claim 20 wherein said second solution is applied to said wetted web of step (1) in an amount such that the total weight of said binder resin or polymer added to said wetted web of step (1) is from about 5 to about 15 percent based on the dry weight of said hydrophobic web.

23. The process of claim 1 wherein the weight ratio of said binder resin or polymer to said precipitating agent in said wetted web of step (2) just prior to said working of said wetted web is from about 4:1 to about 1:1.

24. The process of claim 23 wherein said ratio is from about 2:1 to about 1:1.

25. The process of claim 1 wherein said precipitating agent comprises an anionic precipitating agent.

26. The process of claim 25 wherein said anionic precipitating agent contains anionic groups selected from the class consisting of carboxylate and sulfonate.

27. The process of claim 26 wherein said anionic precipitating agent is a water-soluble, self-catalyzed, thermosetting, acrylic resin.

28. The process of any one of claims 1 to 27 wherein said water-soluble, non-colloidal, cationic, thermosetting binder resin or polymer comprises an epoxy-functional polyamido/polyamino-epichlorohydrin.

29. The process of any one of claims 1 to 27 wherein said water-soluble, non-colloidal, cationic, thermosetting binder resin or polymer comprises an epoxy-functional polyamine-epichlorohydrin containing quaternary ammonium groups.

30. The process of any one of claims 1 to 27 wherein, prior to applying said first solution or dispersion to said web step (1), a mixture comprising water and a wetting agent is applied to said web to prewet said web followed by washing the prewetted web with water to remove said wetting agent while maintaining the web in a water-wetted form.

31. A process for converting a hydrophobic web comprised of polymeric microfibers to a hydrophilic, microfibrous, polymeric filter sheet exhibiting a positive zeta potential comprising:
(1) applying a first solution of a water-soluble, non-colloidal, cationic, thermosetting binder resin or polymer to said web to at least partially wet said web within said first solution;
(2) applying a second solution or dispersion of a precipitating agent to the wetted web of step (1) above to form a web wetted with a mixture of said first solution and said second solution or dispersion;
(3) working the wetted web of step (2) above to mix said first solution and said second solution or dispersion thereby facilitating the precipitation of said binder resin or polymer and the distribution thereof as a coating on the surfaces of the microfibers of the worked web; and
(4) drying the coated web of step (3) above and curing the precipitated binder resin or polymer to provide a hydrophilic, microfibrous, polymeric filter sheet with a positive zeta potential and which is further characterized by the surfaces of the microfibers therein being coated with a cured, precipitated, thermoset, cationic binder resin or polymer.

32. The process of claim 31 wherein said working of the wetted web of step (2) is carried out by contacting said wetted web with a roller rotating counter to the direction said wetted web is moving as the web moves past said roller.

33. The process of claim 32 wherein steps (1), (2) and (3) are carried out in a continuous manner.

34. The process of claim 33 wherein in step (1) said web is saturated with said first solution following which a portion of said first solution is removed from said wetted web of step (1) prior to applying said second solution or dispersion in step (2).

35. The process of claim 31 wherein said drying and said curing in step (4) are carried out at an elevated temperature of from about 50 to about 150 degrees Centigrade for a period of from several minutes to several days.

36. The process of claim 35 wherein said drying and said curing in step (4) are carried out at an elevated temperature of from about 75 to about 130 degrees Centigrade for a period of from about 5 to about 60 minutes.

37. The process of claim 31 wherein said polymeric microfibers of said hydrophobic web are comprised of a polyolefin and said hydrophobic web is prewet with a wetting solution comprising water and a wetting agent prior to step (1) of claim 31.

38. The process of claim 37 wherein said polyolefin is polypropylene.

39. The process of claim 31 wherein said polymeric microfibers of said hydrophobic web are comprised of a polyamide.

40. The process of claim 39 wherein said polyamide is nylon 66.

41. The process of claim 39 wherein said polyamide is nylon 11.

42. The process of claim 31 wherein said polymeric microfibers of said hydrophobic web are comprised of a polyester.

43. The process of claim 42 wherein said polyester is polyethylene terephthalate.

44. The process of claim 42 wherein said polyester is polybutylene terephthalate.

45. The process of claim 31 wherein said hydrophobic web is comprised of microfibers having diameters of from about 0.5 to about 20 micrometers and said hydrophobic web has pore sizes of from about 0.5 to about 80 micrometers.

46. The process of claim 45 wherein said microfibers have diameters of from about 1.0 to about 10 micrometers and said hydrophobic web has an absolute pore rating of from about 0.6 to about 10 micrometers.

47. The process of claim 31 wherein the concentration of said binder resin or polymer in said first solution is in the range of from about 0.1 to about 20 percent.

48. The process of claim 47 wherein the concentration of said binder resin or polymer in said first solution is in the range of from about 0.1 to about 10 percent.

49. The process of claim 48 wherein the concentration of said binder resin or polymer in said first solution is in the range of from about 1 to about 5 percent.

50. The process of claim 49 wherein the concentration of said precipitating agent in said second solution or dispersion is in the range of from about 2.5 to about 7.5 percent.

51. The process of claim 31 wherein said first solution is applied to said web in step (1) in an amount such that the total weight of said binder resin or polymer added to said web in step (1) is from about 1 to about 30 percent based on the dry weight of said hydrophobic web.

52. The process of claim 51 wherein said first solution is applied to said web in step (1) in an amount such that the total weight of said binder resin or polymer added to said web in step (1) is from about 5 to about 15 percent based on the dry weight of said hydrophobic web.

53. The process of claim 31 wherein the weight ratio of said binder resin or polymer to said precipitating agent in said wetted web of step (2) just prior to said working of said wetted web is from about 4:1 to about 1:1.

54. The process of claim 53 wherein said ratio is from about 2:1 to about 1:1.

55. The process of claim 31 wherein said precipitating agent comprises an anionic precipitating agent.

56. The process of claim 55 wherein said anionic precipitating agent contains anionic groups selected from the class consisting of carboxylate and sulfonate.

57. The process of claim 56 wherein said anionic precipitating agent is a water-soluble, self-catalyzed, thermosetting, acrylic resin.

58. The process of any one of claims 31 to 57 wherein said water-soluble, non-colloidal, cationic, thermosetting binder resin or polymer comprises an epoxy-functional polyamido/polyamino-epichlorohydrin.

59. The process of any one of claims 31 to 57 wherein said water-soluble, non-colloidal, cationic, thermosetting binder resin or polymer comprises an epoxy-functional polyamine-epichlorohydrin containing quaternary ammonium groups.

60. The process of any one of claims 31 to 57 wherein, prior to applying said first solution to said web in step (1), a mixture comprising water and a wetting agent is applied to said web to prewet said web followed by washing the prewetted web with water to remove said wetting agent while maintaining the web in a water-wetted form.

61. A microfibrous, polymeric filter sheet comprised of a normally hydrophobic, microfibrous, polymeric web wherein the surfaces of the polymeric microfibers of said web are coated with a cured, precipitated, cationic, thermoset binder resin or polymer, said filter sheet characterized by being hydrophilic and having a positive zeta potential.

62. The filter sheet of claim 61 wherein said polymeric microfibers of said web are comprised of a polyolefin.

63. The filter sheet of claim 62 wherein said polyolefin is polypropylene.

64. The filter sheet of claim 62 wherein said polyolefin is polyethylene.

65. The filter sheet of claim 61 wherein said polymeric microfibers of said web are comprised of a polyamide.

66. The filter sheet of claim 65 wherein said polyamide is nylon 66.

67. The filter sheet of claim 65 wherein said polyamide is nylon 11.

68. The filter sheet of claim 61 wherein said polymeric microfibers of said web are comprised of a polyester.

69. The filter sheet of claim 68 wherein said polyester is polyethylene terephthalate.

70. The filter sheet of claim 61 wherein said polyester is polybutylene terephthalate.

71. The filter sheet of claim 61 wherein the microfibers of said normally hydrophobic, microfibrous, polymeric web have diameters of from about 0.5 to about 20 micrometers.

72. The filter sheet of claim 71 wherein said microfibers have diameters of from about 1.0 to about 10 micrometers.

73. The filter sheet of claim 61 wherein said filter sheet is further characterized by having absolute pore ratings of from about 0.5 to about 80 micrometers.

74. The filter sheet of claim 73 wherein said filter sheet is further characterized by having absolute pore ratings of from about 0.5 to about 10 micrometers.

75. The filter sheet of claim 61 wherein said, cured, precipitated, cationic, thermoset binder resin or polymer is present in an amount of from about 1 to about 30 percent based on the dry weight of said normally hydrophobic, microfibrous, polymeric web.

76. The filter sheet of claim 61 wherein said filter sheet is further characterized by a dry tensile strength of from about 2 to about 15 pounds per inch.

77. The filter sheet of claim 61 wherein said filter sheet has a positive zeta potential over the entire pH range of from about 3 to about 10.

78. The filter sheet of claim 61 wherein said filter sheet is further characterized by having a removal rating of negatively charged particles as low as about 0.1 micrometers or finer.

79. The filter sheet of claim 61 wherein said filter sheet is further characterized by the coating of said cured, precipitated, cationic, thermoset binder resin or polymer being of substantially uniform thickness on the surfaces of the microfibers of said web.

80. The filter sheet of claim 61 wherein said cured, precipitated, cationic, thermoset binder resin or polymer was precipitated with a precipitating agent comprising an anionic precipitating agent.

81. The filter sheet of claim 80 wherein said anionic precipitating agent contained anionic groups selected from the class consisting of carboxylate and sulfonate.

82. The filter sheet of claim 81 wherein said anionic precipitating agent was a water-soluble, self-catalyzed, thermosetting, acrylic resin.

83. The filter sheet of any one of claims 61 to 82 wherein said cured, precipitated, cationic, thermoset binder resin or polymer comprises an epoxy-functional polyamido/polyamino-epichlorohydrin.

84. The filter sheet of any one of claims 61 to 82 wherein said water-soluble, non-colloidal, cationic, thermosetting binder resin or polymer comprises an epoxy-functional polyamine-epichlorohydrin containing quaternary ammonium groups.

85. The filter sheet of claim 61 wherein said filter sheet is in the form of a filter element.

86. The filter sheet of claim 61 wherein said filter sheet has been formed into a pleated form and incorporated into a cartridge.

87. A method for the filtration of particulates from a filter medium comprising passing said medium through the filter sheet of any one of claims 61 to 82, 85 or 86.

88. The method of claim 87 wherein said fluid medium is water.

89. A process for converting a hydrophobic web comprised of polymeric microfibers to a hydrophilic, microfibrous, polymeric filter sheet exhibiting a positive zeta potential comprising:

(1) substantially simultaneously applying (a) a first solution or dispersion of a precipitating agent and (b) a second solution of a water-soluble, non-colloidal, cationic, thermosetting binder resin or polymer to said web to form a web wetted with a mixture of said first solution or dispersion and said second solution;

(2) working the wetted web of step (1) above to mix said first solution or dispersion and said second solution, thereby facilitating the precipitation of said binder resin or polymer and the distribution thereof as a coating on the surfaces of the microfibers of the worked web; and (3) drying the coated web of step (2) above and curing the precipitated binder resin or polymer to provide a hydrophilic, microfibrous, polymeric filter sheet with a positive zeta potential and which is further characterized by the surfaces of the microfibers therein being coated with a cured, precipitated, thermoset, cationic binder resin or polymer.

* * * * *